(12) United States Patent  
Sgro (10) Patent No.: US 8,814,888 B2
(45) Date of Patent: Aug. 26, 2014

(54) SYSTEM FOR PUTTING REINFORCEMENT-FORMING MEANS FOR A SUTURE INTO PLACE

(75) Inventor: Jean-Claude Sgro, Dijon (FR)

(73) Assignee: Sofradim Production, Trevoux (FR)

( * ) Notice: Subject to any disclaimer, the term of this patent is extended or adjusted under 35 U.S.C. 154(b) by 1734 days.

(21) Appl. No.: 11/887,898

(22) PCT Filed: Apr. 6, 2006

(86) PCT No.: PCT/FR2006/050305
§ 371 (c)(1),
(2), (4) Date: Oct. 4, 2007

(87) PCT Pub. No.: WO2006/106269
PCT Pub. Date: Oct. 12, 2006

(65) Prior Publication Data
US 2009/0076528 A1    Mar. 19, 2009

(30) Foreign Application Priority Data
Apr. 7, 2005  (FR) .................................. 05 03463

(51) Int. Cl.
*A61B 17/08*    (2006.01)
(52) U.S. Cl.
USPC ........................................................ 606/151
(58) Field of Classification Search
USPC ................. 606/151–155, 213, 215, 219, 220; 623/11.11, 23.72, 23.75; 600/29, 30, 600/37
See application file for complete search history.

(56) References Cited

U.S. PATENT DOCUMENTS

| | | | | |
|---|---|---|---|---|
| 5,116,357 A | * | 5/1992 | Eberbach | 606/213 |
| 5,122,155 A | * | 6/1992 | Eberbach | 606/213 |
| 5,370,650 A | * | 12/1994 | Tovey et al. | 606/151 |
| 5,503,638 A | * | 4/1996 | Cooper et al. | 623/11.11 |
| 5,542,594 A | * | 8/1996 | McKean et al. | 227/178.1 |
| 5,575,803 A | | 11/1996 | Cooper et al. | |
| 5,634,931 A | * | 6/1997 | Kugel | 606/151 |
| 5,702,409 A | * | 12/1997 | Rayburn et al. | 606/151 |
| 5,766,188 A | * | 6/1998 | Igaki | 606/151 |
| 5,769,892 A | * | 6/1998 | Kingwell | 606/151 |
| 5,810,855 A | * | 9/1998 | Rayburn et al. | 606/151 |
| 5,814,057 A | * | 9/1998 | Oi et al. | 606/151 |
| 5,843,096 A | * | 12/1998 | Igaki et al. | 606/151 |
| 5,902,312 A | * | 5/1999 | Frater et al. | 606/148 |
| 5,908,427 A | * | 6/1999 | McKean et al. | 606/139 |
| 5,922,026 A | * | 7/1999 | Chin | 623/23.72 |

(Continued)

FOREIGN PATENT DOCUMENTS

DE    199 24 311 A1    11/2000
WO    WO 99/02090 A    1/1999

*Primary Examiner* — Dianne Dornbusch
(74) *Attorney, Agent, or Firm* — Kilpatrick Townsend & Stockton LLP (57) ABSTRACT

The invention relates to a placement system for putting into place means that form reinforcement for a suture. The system comprises reinforcement-forming means for reinforcing a zone that is to be sutured, said means comprising a first reinforcement portion and a second reinforcement portion, a catching portion interconnecting said first and second portions of the reinforcement-forming means and serving to take hold of the zone for suturing, and jaw-passing means for passing two jaws of a suture clamp, such that said first portion of the reinforcement-forming means is suitable for facing one of the two jaws and said second portion of the reinforcement-forming means is suitable for facing the other one of the two jaws, said placement system further comprising grip means.

12 Claims, 4 Drawing Sheets

(56) References Cited

U.S. PATENT DOCUMENTS

| | | | |
|---|---|---|---|
| 6,010,447 A * | 1/2000 | Kardjian | 600/29 |
| 6,099,551 A * | 8/2000 | Gabbay | 606/219 |
| 6,273,897 B1 * | 8/2001 | Dalessandro et al. | 606/139 |
| 6,551,356 B2 * | 4/2003 | Rousseau | 623/23.72 |
| 6,599,318 B1 * | 7/2003 | Gabbay | 623/11.11 |
| 6,638,285 B2 * | 10/2003 | Gabbay | 606/151 |
| 6,704,210 B1 * | 3/2004 | Myers | 361/773 |
| 7,048,682 B2 * | 5/2006 | Neisz et al. | 600/30 |
| 7,303,525 B2 * | 12/2007 | Watschke et al. | 600/30 |
| 7,377,928 B2 * | 5/2008 | Zubik et al. | 606/151 |
| 7,665,646 B2 * | 2/2010 | Prommersberger | 227/175.1 |
| 2002/0099258 A1 * | 7/2002 | Staskin et al. | 600/29 |
| 2002/0151762 A1 * | 10/2002 | Rocheleau et al. | 600/30 |
| 2002/0151911 A1 | 10/2002 | Gabbay | |
| 2003/0130670 A1 * | 7/2003 | Anderson et al. | 606/151 |
| 2004/0039453 A1 * | 2/2004 | Anderson et al. | 623/23.72 |
| 2010/0147922 A1 * | 6/2010 | Olson | 227/176.1 |

* cited by examiner

SYSTEM FOR PUTTING REINFORCEMENT-FORMING MEANS FOR A SUTURE INTO PLACE

This is a 371 national phase application of PCT/FR2006/050305 filed 6 Apr. 2006, claiming priority to French Patent Application No. FR 0503463 filed 7 Apr. 2005, the contents of which are incorporated herein by reference.

FIELD OF THE DISCLOSURE

The invention relates to a system for putting reinforcement-forming means for a suture into place.

BACKGROUND

In the context of surgery, when there is a need to section at least a portion of an organ, the surgeon needs to suture the portion of the organ that remains in the patient's body, and possibly also the other portion (which is to be removed or displaced). To do this, the surgeon generally makes use of a suture clamp; suture clamps of known type are generally linear cutting staplers that possess at least one blade or knife and that can be refilled with refills so as to enable several stapling actions to be performed while an operation is taking place. The refills may possibly be of different types, in particular so as to make it possible to have staples of different sizes from one refill to another.

Means that constitute reinforcement for a suture are put into place in order to reinforce the zone that has been sectioned and that runs the risk of being damaged, in particular the risk of being torn under the stapling action, specifically when the organ is a distended or inflamed intestine, or the risk of not being closed off, in particular when pulmonary tissue is involved.

In known reinforcement devices, a sleeve of optionally resorbable fabric surrounds the ends of an automatic suture clamp so that when the staples are put into place, the fabric is engaged by the staples and prevents them from sinking into the zone for treatment.

However such reinforcement sleeves are difficult to keep in position on the jaws of the clamp.

SUMMARY

An object of the invention is to provide a system for putting reinforcement means into place that enables the reinforcement to be held on the suture clamp before the organ for treatment is sectioned, and that enables the reinforcement-forming means to be taken by the suture-forming means at the time the suture-forming means are put into place.

This object of the invention is achieved by the fact that the system comprises reinforcement-forming means for reinforcing a zone that is to be sutured, said means comprising a first reinforcement portion and a second reinforcement portion, with a catching portion interconnecting said first and second portions of the reinforcement-forming means and serving to take hold of the zone for suturing, and jaw-passing means for passing two jaws of a suture clamp, such that said first portion of the reinforcement-forming means is suitable for facing one of the two jaws, and said second portion of the reinforcement-forming means is suitable for facing the other one of the two jaws, said positioning system further comprising grip means formed by two strips connected to the reinforcement-forming means and extending rearwards away from the region of the jaws.

Thus, prior to sectioning, the reinforcement-forming means are held on the suture clamp by the jaw-passing means; while sectioning is taking place and while the suture-forming means are being put into place, the reinforcing means are sutured on the sectioned portion of the organ; then at the end of the operation, after the grip means have been separated, the reinforcement means remain in place.

Furthermore, the catching portion serves to take hold and keep hold of the organ for sectioning, bringing it towards the suture clamp, said catching portion serving to take hold of the zone for suturing and optionally to move it towards the outside of the body of the patient for surgery.

Likewise, the grip means make it easier to put the suture clamp into position in the system, and in particular in the jaw-passing means: these grip-forming means are preferably of a length that is sufficient to enable the surgeon to take hold of them in the hand or in a forceps.

In a first embodiment, said jaw-passing means comprise two openings of closed outline situated respectively in said first and second portions of the reinforcement-forming means and/or the grip means, away from the catching portion.

In a second embodiment, the system further comprises support-forming means and detachable assembly means enabling the reinforcement-forming means and the support-forming means to be assembled together to define said jaw-passing means that are formed by two housings for housing the two jaws of a suture clamp. Together with the support-forming means, the first reinforcement portion forms one of the two housings, while the second reinforcement portion forms the other one of the two housings.

The reinforcement-forming means are thus situated on either side of the organ for sectioning. As a result, when the two jaws of the suture clamp, housed in said housings, press against the organ for sectioning and suturing, the two reinforcement-forming means are facing the organ, which is thus sandwiched between them, thereby enabling the entire sutured zone to be reinforced.

In known manner, when the organ is sectioned in two, both portions of the organ are sutured. It will be understood that the reinforcement-forming means of the invention are to be found after sectioning on both of the two portions of the sectioned and sutured organ.

Under such circumstances, it will be understood that the grip means make it easier to keep the housings in register with the active portions of the clamp and make it easier to withdraw the support-forming means after the reinforcement-forming means have been put into place on the sutured and reinforced zone.

Thus, after the zone for treatment has been sectioned and sutured, the support-forming means of each of the two housings can be withdrawn.

In order to protect the sutured and reinforced zone, provision can be made to cover the suture-forming means that have been put into place by the clamp. To do this, the system preferably includes holder-forming means that serve, after the zone for suturing has been sutured, to hold the first and second reinforcement portions together.

The first and second reinforcement portions are held firstly against the sectioned organ by the suture-forming means and secondly one against the other away from the sutured and reinforced zone, after they have been folded over said zone.

Thus, using such reinforcement-forming means also makes it possible to protect the portion of the organ that remains in place, referred to as a stump, and prevent it from adhering to other tissue so that the stump can be found easily during subsequent surgery which generally takes place three to five weeks later. For example, when the surgery comprises resection of the sigmoid without re-establishing continuity, if the stump is not protected, adhesion becomes organized around it, and in particular a mass is built up of stuck-together loops of the small intestine. During subsequent surgery, it is then necessary to dissect the small intestine loops, running the risk of septicemia by piercing them. Furthermore, it is sometimes possible to re-establish continuity with a celioscope; under such circumstances, if there is too much adhesion, it is necessary to abandon this approach and return to the open approach, which is less advantageous for the patient. Thus, adding the reinforcement-forming means can prevent adhesion forming on the stump, thereby avoiding local infection as well as adhesion.

The holder-forming means may be of any known type, for example adhesive means or fastener means of the self-gripping type (e.g. Velcro®), etc.

Advantageously, the holder-forming means have first holder elements disposed on the first reinforcement portion and second holder elements disposed on the second reinforcement portion, said first and second holder elements being suitable for co-operating to hold said first and second reinforcement portions one against the other.

In order to avoid entraining other organs with the holder-forming means when the reinforcement-forming means are put into place around the organ for sectioning, provision can be made: for the reinforcement-forming means to be in the form of a strip having a first face and a second face, said first face facing towards the inside of the respective housings when the support-forming means and the reinforcement-forming means are assembled together; for the first and second holder means to be disposed on said first face; and after the support-forming means and the reinforcement-forming means have been separated, for the first and second reinforcement portions to be suitable for being folded over in half so that the first and second holder elements can engage mutually so as to hold said first and second reinforcement portions together.

The invention can be well understood and its advantages appear better on reading the following detailed description of embodiments of the invention shown as non-limiting examples.

BRIEF DESCRIPTION OF THE DRAWINGS

The description refers to the accompanying drawings, in which.

DETAILED DESCRIPTION

Figures 1, 2A:
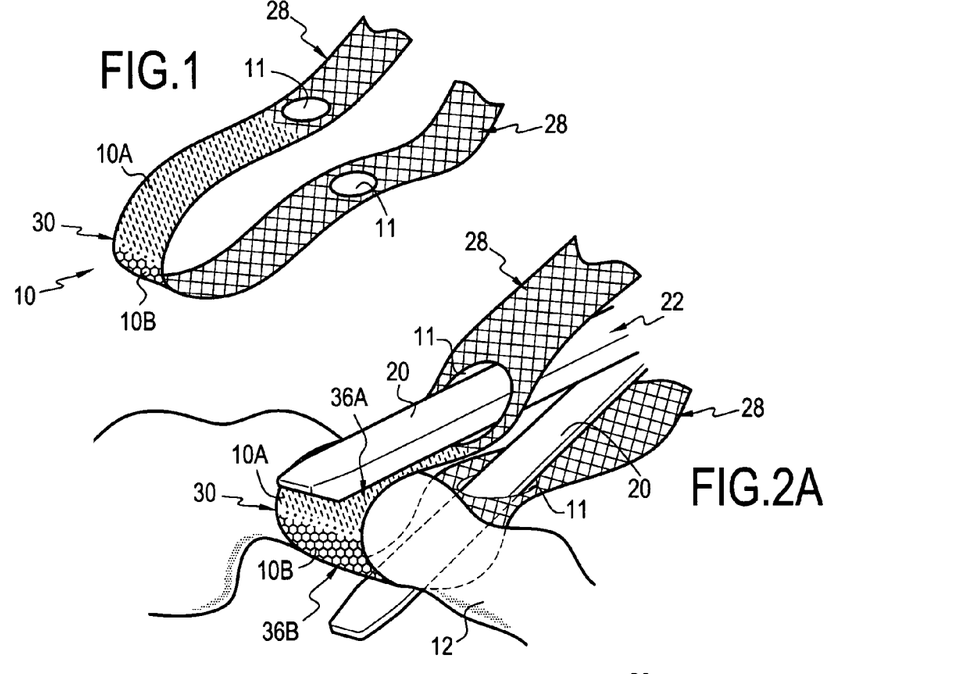
FIG. 1 is a perspective view of the system of the invention in a first embodiment.
FIGS. 2A to 2C are perspective views showing the FIG. 1 system while it is in use.

FIGS. 1 and 2A show a system for putting into place means that form reinforcement for a suture and that constitute a first embodiment comprising reinforcement-forming means 10 for reinforcing at least one zone 12 that is to be sectioned and sutured.

These reinforcement-forming means 10 are made up of a first reinforcing portion 10A and a second reinforcing portion 10B interconnected by a catching portion 30 for taking hold and keeping hold of the zone 12 of the organ, and acting like a tape.

Either the first and second reinforcing portions 10A and 10B are part of a single strip, or else they are attached to each other, e.g. by stitching either directly or else via another piece belonging to the catching portion 30.

The ends of the first and second reinforcement portions 10A and 10B remote from the catching portion 30 are extended by grip means 28 making it easier to grip the reinforcement-forming means 10 and to hold the entire system on the jaws 20 of the suture clamp 22. Specifically, the grip means 28 are formed by two strips, each being formed by the same strip or by a strip other than that forming the first and second reinforcement portions 10A and 10B.

Thus, the grip means 28 are connected to the reinforcement-forming means (10A and 10B) and extend beyond the region of the jaws 20 (to the right in FIG. 2A) so that they can be held in the hand or in a forceps by the surgeon performing the operation or by an assistant.

As can be seen in FIG. 2A, after the catching portion 30 has taken hold of the zone 12 of the organ, the jaws 20 of the clamp 22 are inserted into jaw-passing means, in this example constituted by two openings 11 of closed outline (circular in the drawings) situated at a distance from the catching portion 30, either in the first and second reinforcement portions 10A and 10B, or else in the strip portions forming the grip means 28 (as shown), or else in both the reinforcement-forming means 10 and the grip means 28.

In this way, after catching the zone 12 of the organ, it is possible to insert each jaw 20 of the clamp through a respective opening 11, with the active face of each jaw 20 facing respectively the first and second reinforcement portions 10A and 10B (see FIG. 2A) on either side of the zone 12 of the organ.

When use is made of the suture clamp 22, its two jaws 20 are moved towards each other on either side of the organ 12 for surgery. The organ is then cut into two portions 12A and 12B (see FIG. 2B) which are simultaneously sutured, specifically being stapled by staples 26 stored in the jaws 20 of the suture clamp 22. On sectioning the organ 12, the first and second reinforcement portions 10A and 10B, and also the catching portion 30, are themselves also cut into two substantially identical bands or straps extending as far as the openings 11 in the longitudinal direction parallel to the longitudinal direction of the jaws 20 of the suture clamp 22.

Figure 2B:
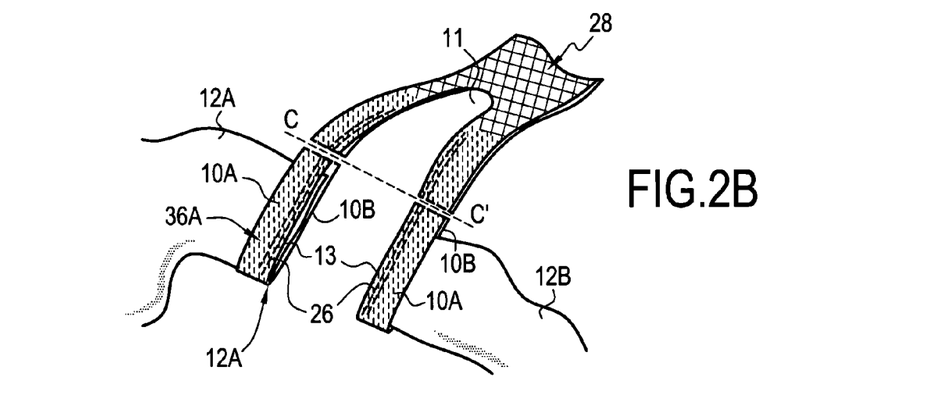

Thus, one strap of the first reinforcement portion 10A and one strap of the second reinforcement portion 10B are then connected to the portion 12A via a suture 13 by means of the staples 26, so as to form the portion 12A' that corresponds to the portion 12A that has been sutured and reinforced.

The portions 12A and 12B are analogous, such that the description below with reference to FIGS. 2B and 2C relates only to the portion 12A.

As can be seen in FIG. 2B, a cut is made along a line C-C', e.g. using scissors, so as to separate the two sutures 13 from the grip means 28. Thus, the sutured and reinforced zone 12A' is separated from the grip means 28 and also from the other portion 12B of the organ.

Figure 2C:
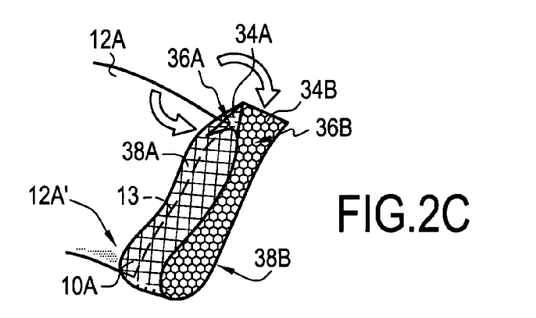

Thereafter, as can be seen in FIG. 2C, the first and second reinforcement portions 10A and 10B are folded over one onto the other (see the arrows) and onto the suture 13, which is thus protected.

More precisely, the first and second reinforcement portions 10A and 10B are assembled together by holder-forming means 34 suitable for co-operating to hold the first and second reinforcement portions 10A and 10B one against the other.

Specifically, the holder-forming means 34 have first holder elements 34A disposed on the first reinforcement portion 10A and second holder elements 34B disposed on the second reinforcement portion 10B.

The first holder elements 34A are disposed on a face 36A of the first reinforcement portion 10A that used to face in the opposite direction relative to the organ 12, when it was still connected to the grip means 28. The same applies to the second holder elements 34B in a face 36B of the second reinforcement portion 10B.

The face 36A is turned towards the suture-forming means (blade and staples 26 of the clamp 22), prior to being put into place on the zone 12 for sectioning and suturing, so as to avoid any snagging while the system is being put into place around the organ. Furthermore, in this configuration, since the first holder elements 34A at the beginning of the operation face in the opposite direction to the second holder elements 34B, they cannot perform their connection function at that moment, because they cannot co-operate with each other.

In FIG. 2C, it can thus be seen that after the first and second reinforcement portions 10A and 10B have been turned over, their faces 36A and 36B respectively carrying the first holder elements 34A and the second holder elements 34B are to be found face to face such that the holder-forming means 34 can then perform their function and achieve assembly. In this position, it is the other faces 38A, 38B of the first and second reinforcement portions 10A and 10B that are to be found facing outwards.

By way of example, the holder-forming means 34 are of the self-gripping type, with the first holder elements 34A being formed of hook-shaped or mushroom-shaped elements and the second holder elements 34B being formed of loop-shaped elements.

Figure 3:
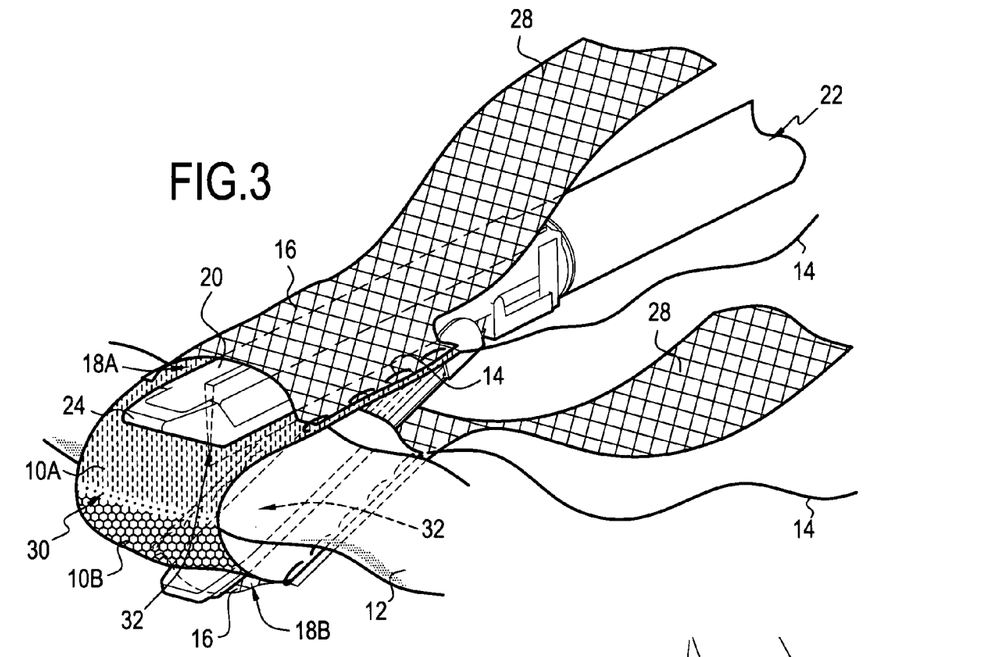
FIG. 3 is a perspective view of the system in a second embodiment.
Figure 4:
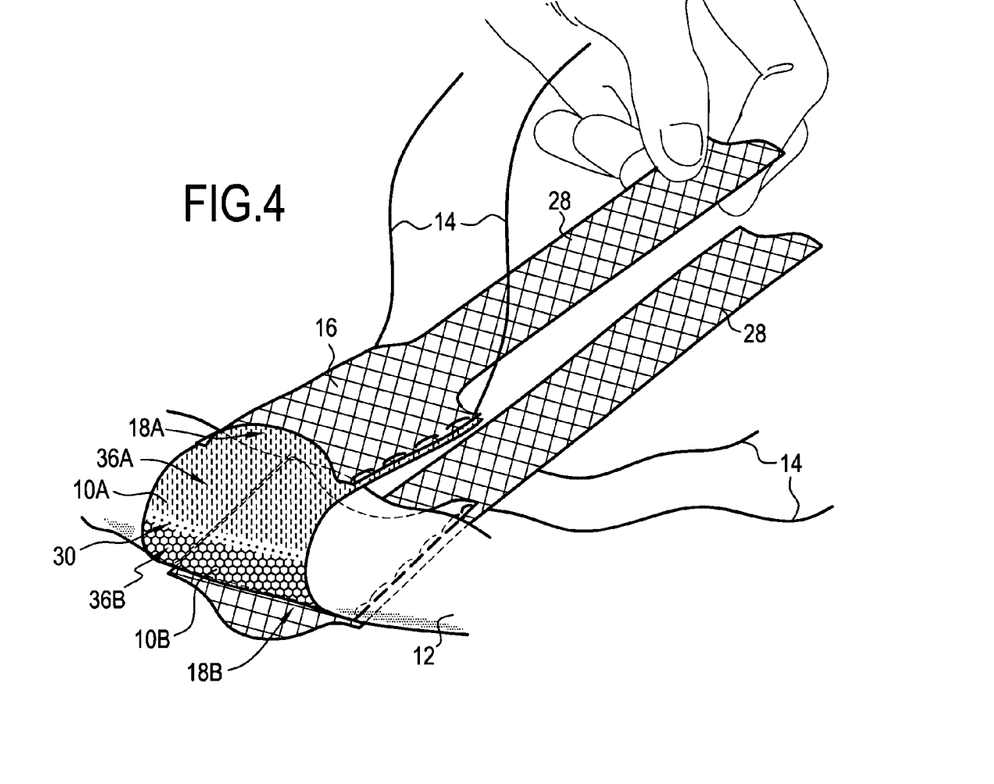
FIG. 4 is a perspective view of the FIG. 3 system put into place around an organ prior to surgery.

Reference is now made to FIGS. 3 and 4 showing a system constituting a second embodiment of the invention.

In this embodiment, the reinforcement-forming means 10 are assembled with the help of detachable assembly means 14 to support-forming means 16 (comprising two strips) so as to form two housings 18A, 18B in which each of the two jaws 20 of a suture clamp 22 of known type can be placed. In order to ensure that the reinforcement means are disposed properly all along the sutured zones, the housings 18A and 18B are preferably through housings, i.e. open at both ends; thus, the free end 24 of the jaw 20 of the suture clamp 22 can project from the reinforcement-forming means 10 and beyond the end of the zone 12.

The reinforcement-forming means 10 are disposed facing the active zone of the jaw 20 of the suture clamp 22, specifically facing the suture-forming means, e.g. comprising firstly staples 26 stored in one of the two jaws 20, and secondly means for folding the staples over, formed in the other one of the two jaws 20, which jaw also includes the blade.

As in the first embodiment, the reinforcement-forming means 10 comprise a first reinforcement portion 10A and a second reinforcement portion 10B, the first reinforcement portion co-operating with the support-forming means 16 to form one of the two housings 18A, while the second reinforcement portion 10B co-operates with the support-forming means 16 to form the other one of the two housings 18B.

In order to make it easier to grip the support-forming means 16 and to hold the entire system on the jaws 20 of the suture clamp 22, grip means 28 are connected to and extend the support-forming means 16.

Specifically, the grip means 28 are formed by a strip that extends rearwards (to the right in the figures) away from the region of the jaws 20, so as to be capable of being held by a hand or by a forceps of the surgeon performing the operation or of an assistant.

Similarly, the assembly means 14 serving to assemble together the reinforcement-forming means 10 and the support-forming means 16 along their longitudinal edges, specifically a thread 14, preferably extends beyond the housing 18 in the vicinity of the grip means 28 so that it can be grasped quickly and easily after the sectioning and suturing operation.

The two housings 18A and 18B shown in FIG. 3 are assembled together via a catching portion 30 that serves to take hold of the organ for surgery and to move it towards the suture clamp 22.

Furthermore, in order to reinforce the two zones that are sectioned and sutured simultaneously with the suture clamp 22, provision can be made for two assembly threads 14 per housing 18A, 18B, as shown in FIG. 3.

Before the operation, as shown in FIG. 4, the system is used to take hold of the organ for surgery by means of the catching portion 30 which acts as a tape. The tape 30 is passed behind the organ for surgery 12, so as to bring it into a region where the surgeon can place the suture clamp 22. While the system of the invention is being put into place, the operator, usually the surgeon, ensures that the first reinforcement portion 10A and the second reinforcement portion 10B are situated facing each other. To do this, it is appropriate to pass the tape 30 behind the portion of the organ 12 on which the operation is to be performed, and then to bring the first and second reinforcement portions 10A and 10B to face each other with the help of the grip means 28.

It is then possible for a suture clamp 22 to be put into place in the system by inserting each of the two jaws 20 of the suture clamp 22 into the respective housings 18A and 18B, as shown in FIG. 3.

In this configuration, after the jaws 20 of the suture clamp 22 have been inserted into the housings 18A and 18B, the facing first and second reinforcement portions 10A and 10B are indeed situated facing the active regions 32 of the jaws 20, i.e. the zones in which the suture-forming means are formed. Specifically, the active regions 32 of one of the two jaws 20 (towards the bottom in FIG. 3) stores the staples 26 prior to use, while the other active region of the other one of the two jaws 20 include the blade and the means for folding over the staples (towards the top in FIG. 3).

Figure 5:
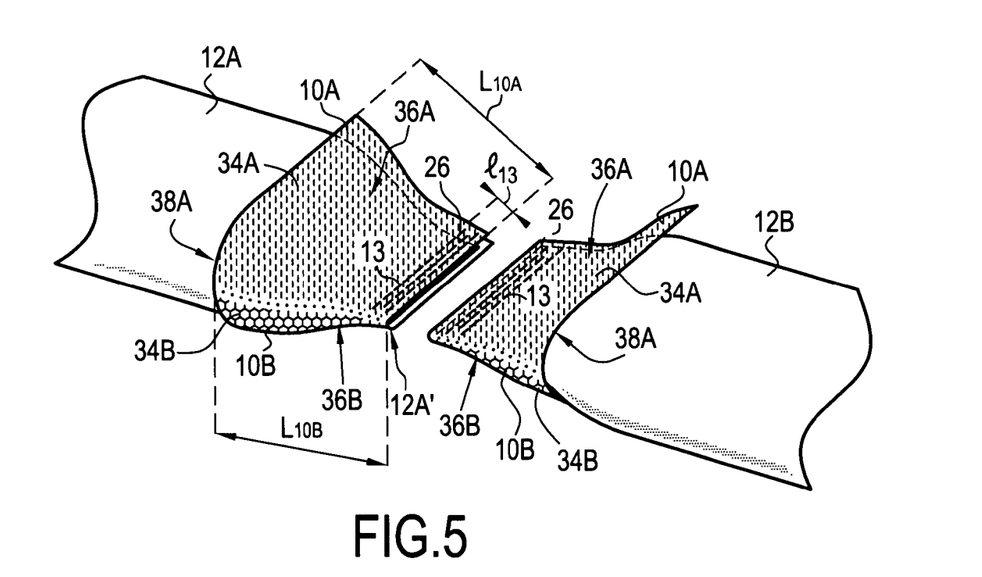
FIG. 5 is a diagrammatic perspective view of sutured and reinforced zones.

When the suture clamp 22 is used, its two jaws 20 are pressed one against the other around the organ 12 for surgery. The organ is then cut into two portions 12A and 12B that are simultaneously sutured, specifically they are stapled using staples 26 stored in the jaws 20 of the suture clamp 22, as shown in FIG. 5. When the organ 12 is sectioned, the first and second reinforcement portions 10A and 10B, and also the tape 30 are likewise cut in two in the longitudinal direction, parallel to the longitudinal direction of the jaws 20 of the suture clamp 22. The portions 12A and 12B are analogous, such that the description below relates only to the portion 12A.

The assembly threads 14 are then withdrawn so as to separate the support-forming means 16 and the grip means 28 from the first and second reinforcement portions 10A and 10B, which at that time are assembled to the portion 12A at a suture 13 by means of staples 26. The support-forming means 16 as separated in this way can then be withdrawn. The grip means 28 facilitate such withdrawal.

The portion 12A' that corresponds to the portion 12A that has been sutured and reinforced, thus has some of the staples 26 previously stored in the active region 32 of one of the jaws 20, and parts of the first and second reinforcement portions 10A and 10B that have been cut into two straps.

Figure 6:
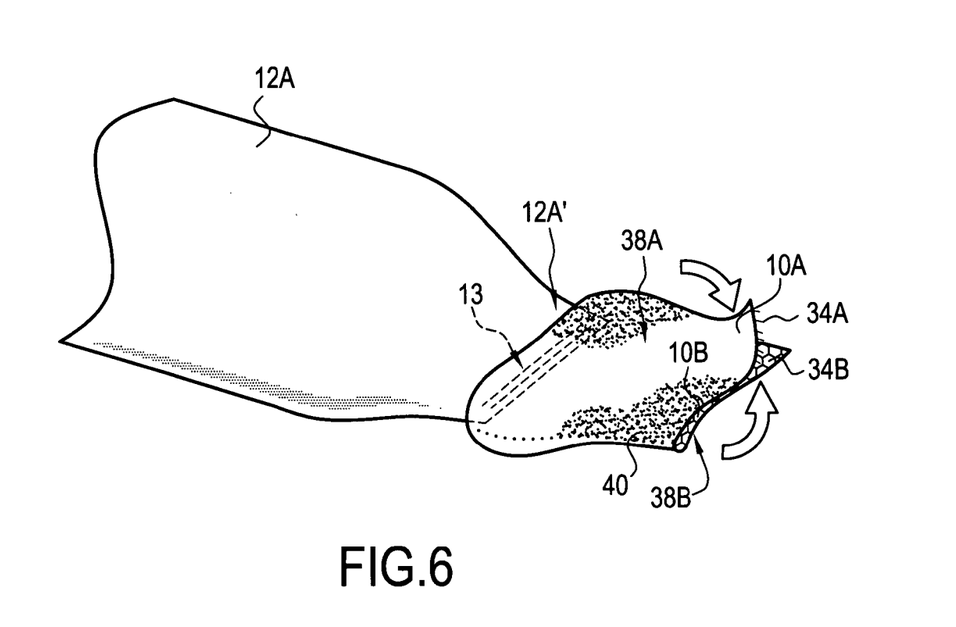
FIG. 6 is a diagrammatic perspective view of a sutured and reinforced zone after overlap.

The first and second reinforcement portions 10A and 10B are then folded over the sutured and reinforced zone 12A', as shown in FIG. 6 so as to be assembled one against the other away from the sutured and reinforced zone 12A'. For this purpose, the first and second reinforcement portions 10A and 10B have holder-forming means 34 suitable for co-operating to hold the first and second reinforcement portions 10A and 10B one against the other.

Specifically, the holder-forming means 34 comprise first holder elements 34A disposed on the first reinforcement portion 10A and second holder elements 34B disposed on the second reinforcement portion 10B.

The first holder elements 34A are disposed on one face 36A of the first reinforcement portion 10A that used to face towards the inside of the housing 18A when it was still connected to the support-forming means 16 (see FIGS. 3 and 4). This face 36A is turned towards the suture-forming means 26 before being put into place on the zone 12 for sectioning and suturing, so as to avoid snagging while the system is being put into place around the organ. In addition, in this configuration, since the holder-forming means 34 at the beginning of the operation face towards the inside of the housing 18A, they are prevented at that time from performing their function since they cannot co-operate.

In order to facilitate putting the system into place against the organ for surgery, a second face 38A of the first reinforcement portion 10A that is firstly opposite from the first face 36A having the holder elements 34A and secondly faces towards the outside of the housing 18A, preferably includes a non-stick material, for example a lubricating material. The same applies to a second face 38B of the second reinforcement portion 10B that is opposite from the first face 36B having the holder elements 34B and that faces outwards from the housing 18B. Specifically, the non-stick material comprises a lubricating non-stick compound 40, in particular of the gelatin type for facilitating insertion of the system around the organ 12 for surgery and for preventing any anatomical adhesion.

After sectioning and suturing, as shown in FIG. 5, the first holder elements 34A are situated on the face 36A opposite from the face 38A that then faces the sutured and reinforced zone 12A'.

The respective faces 36A and 36B of the first and second reinforcement portions 10A and 10B are then folded towards each other (see the arrows in FIG. 6) so that the first and second holder elements 34A and 34B can co-operate to keep the first and second reinforcement portions 10A and 10B one against the other. Once put into place, the respective opposite faces 38A and 38B coated in a non-stick compound 40 thus constitute the visible faces of the system.

Figure 7:
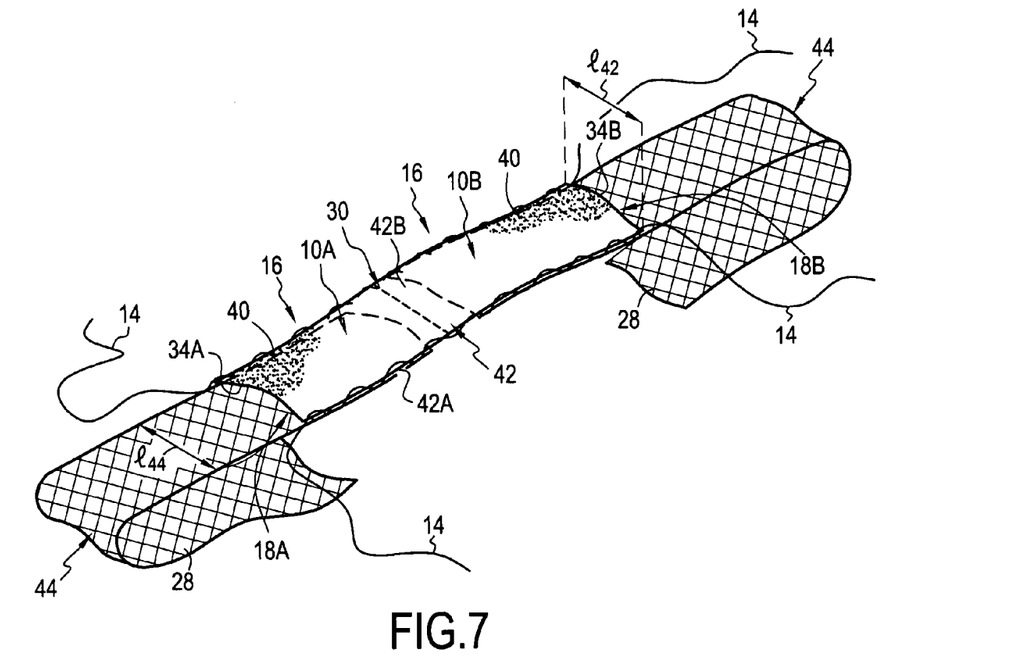
FIG. 7 is a perspective view of a variant embodiment of the system.

FIG. 7 shows a system made up of strips that are assembled together. Specifically, the reinforcement means 10 are formed by a first strip of biocompatible fabric 42, specifically made of a resorbable biocompatible material. This fabric presents a face 42B having a lubricating material 40 as mentioned above, and an opposite face 42B having the holder-forming means 34A and 34B, as described above.

For reasons of expense, the lubricating material and the holder-forming means need be provided only in those zones of the fabric that require them to be present. It will be understood that the holder-forming means need be provided only in the zone of the strip 42 that is to be folded over as shown in FIG. 6. There is no need for the zone that is to be stapled by the suture 13 also to have holder-forming means, since they will not be able to perform their function.

This strip of fabric 42 forms both the first and second reinforcement portions 10A and 10B of the tape 30. It will be understood that the first and second reinforcement portions 10A and 10B, and the tape 30, could also be made up of two or three distinct elements that are connected together. Under such circumstances, the elements could be made of different materials, providing they are always bioresorbable materials.

The strip of fabric 42 is also assembled at each of its two ends to two respective strips of fabric 44 made of biocompatible material. Each of these two fabric strips 44 constitute both the support-forming means 16 and the grip-forming means 28 as described above.

These three fabric strips 42, 44, and 44 are connected together by assembly means 14, specifically two releasable threads 14 that are disposed longitudinally on either side of the width of the strips 42 and 44. As described above, these threads 14 are of a length suitable for enabling them to be grasped in the vicinity of the above-mentioned grip means 28. After the operation, it is appropriate merely to pull on the two respective ends of the two threads 14 so as to separate the reinforcement-forming means from the support-forming means, and to withdraw them by taking hold of the grip means 28.

It will be understood that the size of the reinforcement-forming means can be adapted to the size of the zone that is to be sutured. In particular, the width l42 of the strip 42 may be equal to the width l44 of the strip 44 or it may be greater than or smaller than said width. Furthermore, the length of the strip 42 is selected in such a manner that after sectioning and suturing, as shown in FIG. 6, there remains sufficient fabric for folding the first and second reinforcement portions 10A and 10B one against the other over the suture 13. By way of example, the length of the strip 42 can be adapted so that after sectioning and suturing, the lengths L10A and L10B (shown in FIG. 5) are not less than twice the width l13 of the suture 13.

Care is taken to ensure that the width l42 of the strip 42 and the lengths L10A and L10B are also selected as a function of the size of the jaws 20 of the suture clamp 22 that is used.

Figure 8:
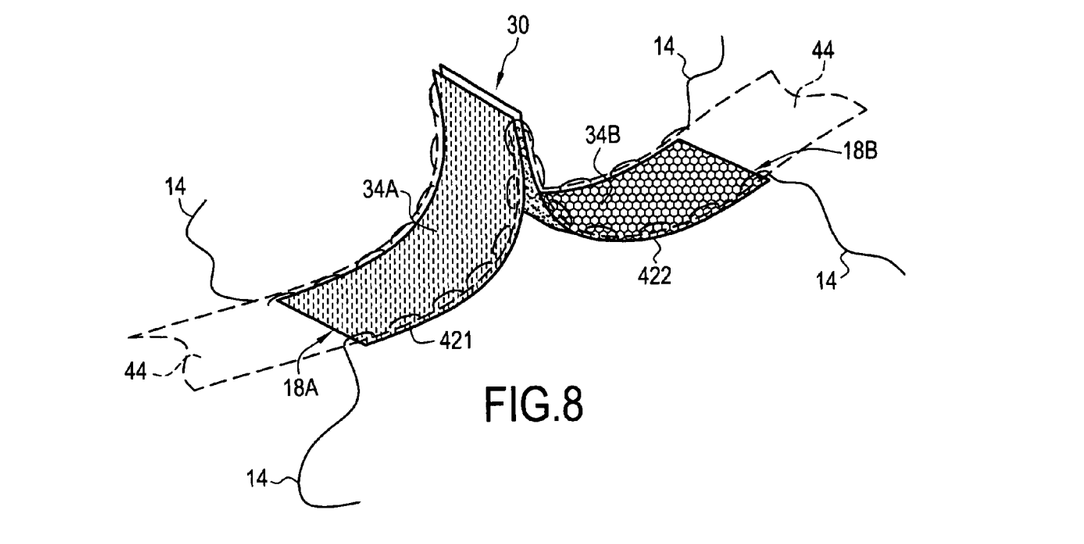
FIG. 8 is a perspective view of the system in another variant embodiment.

In a variant embodiment shown in FIG. 8, the system for putting the reinforcement-forming means of a suture into place is made up of four strips: the two strips 44 of the FIG. 7 system (in dashed lines) and two strips 421 and 422 corresponding to the single strip 42 of FIG. 7 and forming the first and second reinforcement portions 10A and 10B. These four strips define two housings 18A and 18B with the faces of the two strips 421 and 422 that carry the first and second holder elements 34A and 34B facing towards the insides of those housings. In the example shown in FIG. 8, the four strips are interconnected by only two threads 14 which suffice to hold together the system and to form the catching portion 30 at the adjacent ends of the strips 421 and 422.

What is claimed is:
1. A placement system for putting reinforcement-forming means for a suture into place, the system comprising
    reinforcement-forming means for reinforcing a zone that is to be sutured, said means comprising a first reinforcement portion and a second reinforcement portion,
    with a catching portion interconnecting said first and second portions of the reinforcement-forming means and serving to take hold of the zone for suturing, and jaw-passing means for passing two jaws of a suture clamp, such that said first portion of the reinforcement-forming means is suitable for facing one of the two jaws, and said second portion of the reinforcement-forming means is suitable for facing the other one of the two jaws, said placement system further comprising grip means formed by two strips connected to the reinforcement-forming means;

wherein the two jaws of the suture clamp comprise two opposing jaws with:

one end of each jaw attached to the opposing jaw at a hinge;

the non-hinged end of each jaw is a distal end; and each jaw comprises an outer surface and an inner surface, the outer surface facing away from the opposing jaw and the inner surface facing towards the opposing jaw;

wherein the catching portion is positioned at the distal end of the jaws and the two strips connected to the reinforcement-forming means extend along the outer surface of each jaw from the distal end towards and beyond the hinge.

2. A system according to claim 1 further comprising support-forming means and detachable assembly means enabling the reinforcement-forming means and the support-forming means to be assembled together to define said jaw-passing means that are formed by two housings for housing the two jaws of the suture clamp, and together with the support-forming means, the first reinforcement portion forms one of the two housings, while the second reinforcement portion forms the other one of the two housings.

3. A system according to claim 2, wherein the reinforcement-forming means are in the form of a strip having a first face and a second face, said first face facing towards the inside of the respective housings when the support-forming means and the reinforcement-forming means are assembled together, in that the first and second holder means are disposed on said first face, and in that, after the support-forming means and the reinforcement-forming means have been separated, the first and second reinforcement portions are suitable for being folded over in half so that the first and second holder elements can engage mutually so as to hold said first and second reinforcement portions together.

4. A system according to claim 3, wherein the second face opposite from the face having the holder elements includes a non-stick material.

5. A system according to claim 4, wherein the non-stick material comprises a lubricating non-stick compound.

6. A system according to claim 2, wherein the grip means are connected to the support-forming means.

7. A system according to claim 2, wherein the support-forming means are made of biocompatible material.

8. A system according to claim 2, wherein the two housings are through housings.

9. A system according to claim 1, the system including holder-forming means serving, after the zone for suturing has been sutured, to hold the first and second reinforcement portions together.

10. A system according to claim 9, wherein the holder-forming means have first holder elements disposed on the first reinforcement portion and second holder elements disposed on the second reinforcement portion, said first and second holder elements being suitable for co-operating to hold said first and second reinforcement portions one against the other.

11. A system according to claim 1, wherein the reinforcement-forming means are made of biocompatible material.

12. A system according to claim 11, wherein the biocompatible material is resorbable.

* * * * *